US005728063A

United States Patent [19]
Preissman et al.

[11] Patent Number: 5,728,063
[45] Date of Patent: Mar. 17, 1998

[54] HIGH TORQUE BALLOON CATHETER

[75] Inventors: Howard E. Preissman, Los Gatos; Richard S. Jaraczewski, Livermore; Erin McGurk, Palo Alto, all of Calif.

[73] Assignee: Micro International Systems, Inc., Sunnyvale, Calif.

[21] Appl. No.: 562,565

[22] Filed: Nov. 24, 1995

Related U.S. Application Data

[63] Continuation-in-part of Ser. No. 344,183, Nov. 23, 1994, abandoned.

[51] Int. Cl.$^6$ ................................................. A61M 29/00
[52] U.S. Cl. ............................................... 604/96; 604/282
[58] Field of Search ........................... 604/96, 97, 99, 604/98, 103, 104, 264, 280, 282

[56] References Cited

U.S. PATENT DOCUMENTS

| | | |
|---|---|---|
| 3,416,531 | 12/1968 | Edwards . |
| 3,924,632 | 12/1975 | Cook . |
| 4,418,688 | 12/1983 | Loeb . |
| 4,425,919 | 1/1984 | Alston, Jr. et al. ............... 604/282 X |
| 4,586,923 | 5/1986 | Gould et al. . |
| 4,636,346 | 1/1987 | Gold et al. . |
| 4,637,396 | 1/1987 | Cook . |
| 4,734,093 | 3/1988 | Bonello et al. . |
| 4,739,768 | 4/1988 | Engelson . |
| 4,764,324 | 8/1988 | Burnham . |
| 4,817,613 | 4/1989 | Jaraczewski et al. . |
| 4,899,787 | 2/1990 | Ouchi et al. . |
| 4,921,478 | 5/1990 | Solano et al. . |
| 4,943,275 | 7/1990 | Stricker . |
| 4,964,853 | 10/1990 | Sugiyama et al. . |
| 4,981,478 | 1/1991 | Evard et al. ............................. 604/282 |
| 4,983,166 | 1/1991 | Yamawaki . |
| 5,002,556 | 3/1991 | Ishida et al. . |
| 5,045,072 | 9/1991 | Castillo et al. . |
| 5,057,092 | 10/1991 | Webster, Jr. . |
| 5,061,257 | 10/1991 | Martinez et al. . |

(List continued on next page.)

FOREIGN PATENT DOCUMENTS

| | | |
|---|---|---|
| 0 427 429 A2 | 10/1990 | European Pat. Off. . |
| 0 564 747 A1 | 4/1992 | European Pat. Off. . |
| 0 555 088 A2 | 2/1993 | European Pat. Off. . |
| 3818279 C2 | 12/1990 | Germany . |
| 1509981 A1 | 9/1989 | U.S.S.R. . |
| WO 91/04068 | 4/1991 | WIPO . |
| WO 91/17782 | 11/1991 | WIPO . |
| WO 93/02733 | 2/1993 | WIPO . |
| WO 94/01047 | 1/1994 | WIPO . |
| WO 94/07549 | 4/1994 | WIPO . |

OTHER PUBLICATIONS

"Diagnostic & Interventional Products," Radiology Cardiology and Surgery, Catalog 1982–84.

Daniel A. Rüfenacht, Richard E. Latchaw, "Principles and Methodology of Intracranial Endovascular Access," Neuroimaging Clinics of North America, vol. 2, No. 2, May 1992.

*Primary Examiner*—Michael Powell Buiz
*Assistant Examiner*—N. Kent Gring
*Attorney, Agent, or Firm*—Townsend and Townsend and Crew LLP

[57] ABSTRACT

A balloon catheter (2) comprises an outer sheath (3) housing an inner catheter (10). The inner catheter comprises an inner tubular member (30), a braided reinforcement layer (32), and a soft outer layer (34). The inner tubular member extends from a proximal end (15) of the inner catheter to a first distal location (22). The braided reinforcement layer extends from the proximal end to a second distal location (18), usually located proximal of the first distal location. The soft outer layer extends from the proximal end of the inner catheter to the tip (44) of the inner catheter. In this way, a catheter having a shaft region (16), a transition region (20), and a distal region (24), each with different strength and flexibility characteristics, can be used with the outer sheath. The balloon (8) is bonded to the distal ends of the outer sheath and the inner catheter and is inflated through the space defined therebetween.

27 Claims, 3 Drawing Sheets

U.S. PATENT DOCUMENTS

| | | |
|---|---|---|
| 5,078,681 | 1/1992 | Kawashima . |
| 5,078,702 | 1/1992 | Pomeranz . |
| 5,100,379 | 3/1992 | Wendell . |
| 5,102,415 | 4/1992 | Guenther et al. . |
| 5,250,069 | 10/1993 | Nobuyoshi et al. ................ 604/96 X |
| 5,254,107 | 10/1993 | Soltesz . |
| 5,267,954 | 12/1993 | Nita . |
| 5,290,230 | 3/1994 | Ainsworth et al. . |
| 5,290,232 | 3/1994 | Johnson et al. . |
| 5,290,306 | 3/1994 | Trotta et al. . |
| 5,304,135 | 4/1994 | Shonk . |
| 5,308,325 | 5/1994 | Quinn et al. . |
| 5,324,255 | 6/1994 | Passafaro et al. . |
| 5,571,073 | 11/1996 | Castillo ................................ 604/282 |

HIGH TORQUE BALLOON CATHETER

CROSS REFERENCE TO RELATED APPLICATION

This application is related to U.S. patent application Ser. No. 08/151,320 filed Nov. 12, 1993 titled Small Diameter, High Torque Catheter now abandoned, the disclosure of which is incorporated by reference. This application is a continuation-in-part of application Ser. No. 08/344,183, filed on Nov. 23, 1994 now abandoned, the full disclosure of which is incorporated herein by reference.

BACKGROUND OF THE INVENTION

1. Field of the Invention

The present invention relates generally to medical balloon catheters and methods for their fabrication. More particularly, the present relates to the construction of both large and small diameter, braid-reinforced balloon catheters having controlled flexibility, a soft distal tip and an elastomeric balloon at the tip for the partial or total occlusion of a vessel; the invention can be used for a wide variety of medical applications, such as interventional cardiological or neuroradiology procedures, but are particularly useful for intercranial selective catheterization.

Medical catheters exist for a wide variety of purposes, including diagnosis, interventional therapy, drug delivery, drainage, perfusion, and the like. Catheters for each of these purposes can be introduced to numerous target sites within a patient's body by guiding the catheter through the vascular system, and a wide variety of specific catheter designs have been proposed for different uses.

Of particular interest to the present invention, small diameter tubular access catheters are presently being used for diagnostic and interventional neurological techniques, such as the imaging and treatment of aneurysms, tumors, arteriovenous malformations/fistulas, and the like. The neurological vasculature places a number of requirements on the catheters which are to be employed. The primary requirement is size. The blood vessels in the brain are frequently as small as several millimeters, or less, requiring that the catheters have an outside diameter as small as one French (1 F; 0.33 millimeters). In addition to small size, the brain vasculature is highly tortuous, requiring that neurological catheters be very flexible, particularly at their distal ends, to pass through the regions of tortuosity. Difficulties in endovascular positioning, however, make it desirable to impart high tensile and column strength over at least the proximal portion of the catheter. Additionally, the blood vessels of the brain are relatively fragile, so it is desirable that the catheter have a soft, non-traumatic exterior to prevent injury.

In an effort to meet at least some of these requirements, the small-diameter, variable flexibility catheters, such as Tracker® infusion catheters available from Target Therapeutics, Fremont, Calif., have been developed. Although generally successful, the Tracker® catheters suffer from certain deficiencies. In particular, to achieve high flexibility, tensile strength and catheter wall integrity have been compromised. The Tracker® catheters thus lack both column strength and hoop strength and have a tendency to kink and collapse when passing around small diameter bends. Directability and torqueability of the Tracker® catheters is also limited, and the most flexible distal regions of the catheter are subject to rupture and perforation.

It would therefore be desirable to provide improved small diameter, flexible catheters suitable for introduction to very small blood vessels, particularly to the neurological vasculature. Such catheters should provide sufficient flexibility to permit access to the tortuous regions of the neurological vasculature, while retaining sufficient tensile, column, and hoop strengths to enhance resistance to kinking and collapse. The improved catheters should also have enhanced positioning characteristics, including pushability and torqueability. Additionally, it would be desirable to have an improved wall strength over a portion or all of the catheter wall to resist perforation and failure when introducing high pressure fluids and/or introducing thrombogenic coils and other devices through the catheter.

2. Description of the Background Art

U.S. Pat. No. 4,739,768, describes a catheter consisting of an inner layer and an outer layer, where the inner layer terminates proximally of the outer layer to form a relatively more flexible distal end. WO 91/17782 describes a catheter having a braid-reinforced distal end with a low friction surface. WO 93/02733 describes a catheter having four regions of different stiffness. Braid and otherwise reinforced catheter structures are described in U.S. Pat. Nos. 3,416,531; 3,924,632; 4,425,919; 4,586,923; 4,764,324; 4,817,613; 4,899,787; 5,045,072; 5,057,092; 5,061,257; and EP 555 088. Catheters having soft tips are described in U.S. Pat. Nos. 4,636,346 and 5,078,702. A torque control catheter comprising stainless steel braid-reinforced polyethylene is described in Catalog 1982-84 *"Radiology, Cardiology and Surgery,"* page 16, Cook Inc. The requirements and considerations for constructing catheters and other system components for intercranial selective catheterization are described in Rüfenacht and Latchaw (1992) INTER. NEURORAD. 2:251–268. U.S. Pat. No. 4,921,478 to Solano et al. shows a cerebral balloon catheter having an open central lumen and a specially shaped balloon.

SUMMARY OF THE INVENTION

A balloon catheter constructed in accordance with the principles of the present invention comprises an outer sheath, an inner catheter, an annular balloon mounted to and circumscribing the distal ends of the outer sheath and inner catheter, an inflation port at the proximal end of the outer sheath and an inflation passage as defined between the outer sheath and the inner catheter which fluidly couples the inflation port and the balloon. The outer sheath and inflation port are generally conventional. The balloon is usually made of an elastomeric (distensible) material, preferably of silicone rubber, and is preferably bonded to the tips of the outer sheath and the inner catheter. In some cases, it may be desirable to form the balloon from an inelastic (nondistensible) material, such as polyethylene pterephthalate, particularly if the balloon is to be used for dilation.

The inner catheter includes a catheter body including an inner tubular member, a braided reinforcement layer disposed over the inner tubular member, and a soft outer layer formed over the braided reinforcement layer. The flexibility of the catheter body is controlled by selecting the relative lengths and mechanical characteristics of each of these components. The inner tubular member extends a first length with the braided reinforcement layer usually terminating proximally of the distal end of the inner tubular member, preferably by distance in the range from about 0 cm to 20 cm, more preferably from 1 cm to 10 cm, most preferably from 3 cm to 10 cm. The soft outer layer may terminate distally of the distal end of the inner tubular member, preferably by a distance in the range from about 0 cm to 10 cm, more preferably from 1 cm to 10 cm, and most preferably from 1 cm to 3 cm. In this way, up to three distinct regions of flexibility, tensile strength, column strength, and hoop strength may be provided. In addition or as an alternative to terminating the layers at different locations relative to each other, flexibility, tensile strength, column strength, and hoop strength may be varied by selectively controlling the mechanical characteristics of one or more of the individual layers. In particular, the pitch and other braid characteristics of the braided reinforcement layer may be varied to provide increased strength properties along the proximal portions of the catheter body and increased flexibility over the distal portion of the catheter body. The use of the braided reinforcement layer in the catheters of the present invention is particularly advantageous since it provides substantial tensile, column, and hoop strengths with minimum loss of flexibility.

In the exemplary embodiment, a major portion of the catheter body extending from its proximal end to the termination of the braided reinforcement area is the least flexible, but has excellent torque transmission and hoop strength characteristics. The region of the catheter distal to the braid termination but proximal to the termination of the inner tubular member has enhanced flexibility while retaining adequate torqueability and hoop strength to permit guiding of the catheter over a guide wire and prevent kinking and collapse of the catheter lumen. The distal-most region of the catheter comprises only the soft outer layer and possesses the greatest flexibility with the minimum torqueability and hoop strength, and the catheters of the present invention are suitable for introduction to remote, tortuous regions of the brain vasculature.

In a first particular aspect of the present invention, the inner tubular member is composed of a lubricious material, such as a fluorocarbon polymer, polyamide, a polyolefin, a polyimide, or the like, preferably being formed from polytetrafluoroethylene (PTFE). The use of such materials provides a very smooth surface for introducing devices and high velocity fluids through the lumen defined by the inner tubular member. The catheter of the present invention includes only a single transition from the inner tubular member to the contiguous lumen defined by the soft outer layer which extends beyond the distal termination of the inner tubular member.

In a second preferred aspect of the present invention, the braided reinforcement layer is composed of a filament braid, preferably a stainless steel braid, which is annealed and transversely cut at its distal end to remove any protrusions, burrs, discontinuities, or the like, which may result from the termination of braiding. Such discontinuities in the braid at the distal end (or elsewhere) are unacceptable as they would expose the vasculature to trauma, even when covered by the soft outer layer. Previous catheter constructions have generally relied on covering braid terminations with a ring or other protective structure. The present invention minimizes the need for any additional structure at braid termination by use of the unique annealing and cutting process, as described in more detail hereinafter. However, it has been found useful to use a ring of PET heat shrink material to cover the braid terminations.

In a third particular aspect of the present invention, the material of the soft outer layer has a hardness in the range from 30 A to 72 D, and is preferably selected from the group consisting of polyamide polyether block copolymer (Pebax®), polyurethane, silicone rubber, nylon, and the like.

In a fourth particular aspect of the present invention, the inner catheter consists essentially of the inner tubular member, the braided reinforcement layer, and the soft outer layer, as described above, and is free from other structural components which would change the essential mechanical and structural characteristics of the catheter, particularly with regard to flexibility, torque transmission, and softness of the exterior. Such catheter bodies may, however, include other components which do not affect the essential mechanical and structural characteristics, such as proximal connectors, proximal housings, radiopaque markers, and the like.

In a fifth particular aspect of the present invention, the inner catheter further comprises a less stiff reinforcement layer, typically a helically wound ribbon reinforcement layer, that extends distally from the braided reinforcement layer to provide a transition stiffness within the balloon that is less than that of the region comprising the braided reinforcement layer. Usually, the braided reinforcement layer will terminate from 2 cm to 20 cm proximally of the distal end of the inner catheter, more usually from 3 cm to 10 cm proximally of the distal end.

In a sixth particular aspect of the present invention, the outer sheath comprises a reinforcement layer, preferably a helically wound ribbon reinforcement layer which, preferably, extends from the proximal end to the distal end thereof. The reinforcement layer inhibits collapse of the sheath and blockage of the inflation lumen that might otherwise occur during normal use.

In a sixth particular aspect of the present invention, a soft, atraumatic distal tip is secured to the distal end of the inner catheter, with the tip extending distally of the balloon. The tip is preferably unreinforced, but may include a radiopaque marker.

According to a method of the present invention, the inner catheter may be fabricated by providing an inner tubular member, preferably having the characteristics described above. A braid is formed over the inner tubular member from the proximal end to a location spaced proximally from the distal end of the inner tubular member by a distance in the range from 0 cm to 10 cm, preferably from 1 cm to 10 cm, and more preferably from 1 cm to 3 cm. A soft outer layer is then formed over the resulting assembly from its proximal end and extending distally beyond the distal end thereof by a distance in the range from 0 cm to 10 cm (when extending distally beyond the inner tubular member). The soft outer layer further defines a distal lumen which is contiguous with the lumen of the inner tubular member. Preferably, each of the above-fabrication steps occurs while the inner tubular member is disposed over a mandrel which supports the inner tubular member and extends beyond the distal end of said member.

The braid is formed from stainless steel ribbon or other suitable material, typically as a one-over-one or two-over-two braid. After the braid is formed over the inner tubular member and the distal end terminated, the braid is translated distally to extend beyond the mandrel. The braid is then annealed, typically by heating, and the annealed braid filaments cut transversely to form a square-cut end which is free from protrusions, burrs and other discontinuities. The braid is then translated proximally back over the inner tubular member to the desired position space proximally from the distal end thereof. The soft outer layer is then formed over the braid and extending beyond the distal end of the inner tubular member on to the mandrel. Preferably, the soft outer layer is formed by first placing a preformed tube of the desired soft material over the assembly of the braid and inner tubular member and thereafter placing a heat shrink tube over the soft outer layer tubular material. The entire assembly is then heated to a temperature which melts the soft outer layer of material and which constricts the heat shrink tube over the assembly, thus applying pressure to the soft outer layer material. After cooling, the heat shrink tube can be cut from the catheter, and the distal end trimmed to a desired length. Optionally, a proximal connector can be attached to the proximal end of the catheter body.

Other features and advantages of the invention will appear from the following description in which the preferred embodiments have been set forth in detail in conjunction with the accompanying drawings.

DESCRIPTION OF THE PREFERRED EMBODIMENT

Figure 1:
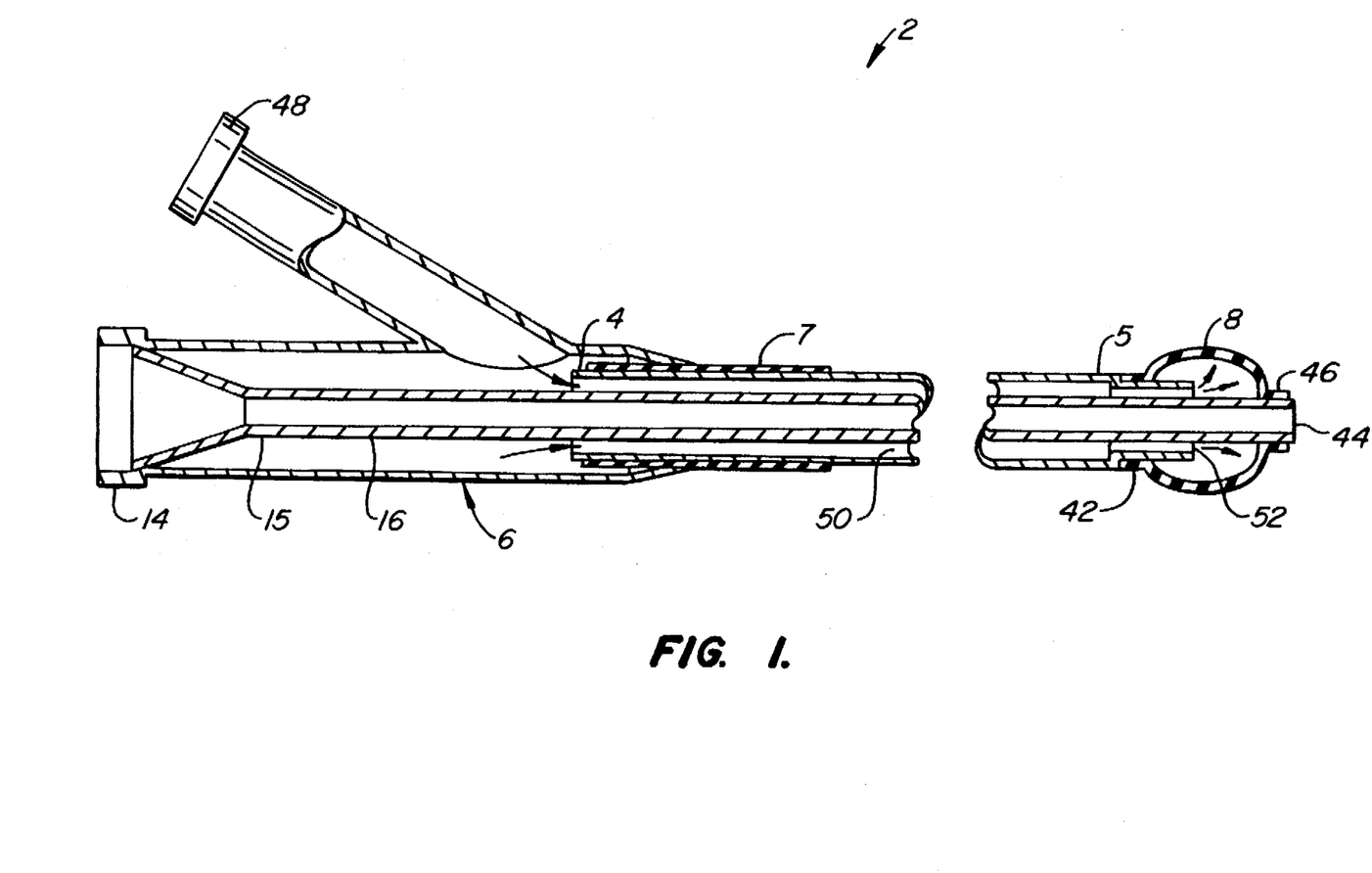
FIG. 1 is a simplified side view showing a balloon catheter made according to the invention.

FIG. 1 illustrates a simplified side view of a balloon catheter made according to the invention. Balloon catheter 2 includes an outer sheath 3 made of, for example, Pebax®, a polyamide polyether block copolymer, having a proximal end 4 and a distal end 5. An injection port assembly 6 is mounted to proximal end 4 through a strain relief 7. An annular, elastomeric balloon 8 is secured to distal end 5 of outer sheath 3 and to an inner catheter 10 housed within outer sheath 3 as will be discussed in more detail below. Injection port assembly 6 includes a connector 14 coupled to the proximal end 15 of inner catheter 10. The specific construction and materials of sheath 3, elastomeric balloon 8, and injection port assembly 6 are generally conventional. The specific construction of inner catheter 10 will now be discussed in detail.

The present invention provides an improved construction for inner catheters of the type having an elongated catheter body with a central lumen extending from proximal end to a distal end thereof. See FIGS. 2 and 3. Such constructions are particularly useful for forming very small diameter catheters, having outside diameters of 4 mm (12 F) preferably below 2.67 mm (8 F), and frequently as small as 1 mm (3 F), and below, such as those used in neurological diagnostic and interventional procedures. Such small catheters will also be useful for other procedures, such as gynecological procedures, cardiac procedures, general interventional radiology procedures, and the like, for access to the small vasculature as necessary. Constructions of the present invention, however, are not limited to such small diameter catheters, and will be useful for larger diameter catheters as well, such as vascular guiding catheters which may have outside diameters larger than 4 mm.

Inner catheters according to the present invention will comprise a catheter body having dimensions and a geometry selected for the intended use. The catheter body will typically have a length in the range from about 40 cm to 200 cm, usually having a length in the range from about 60 cm to 175 cm. The outside diameter of the catheter body will typically be in the range from about 0.33 mm (1 F) to 4 mm (12 F), usually being in the range from about 0.66 mm (2 F) to about 2.66 mm (8 F). The catheter body will define an inner lumen typically having a diameter in the range from about 0.1 mm to 3.6 mm, usually being in the range from about 0.3 mm to 2.5 mm, with catheters having larger outside diameters usually having larger lumen diameters. For the preferred microcatheters of the present invention, the catheter body will have a length in the range from about 80 cm to 150 cm, an outside diameter in the range from about 0.66 mm to 1.75 mm, and an inside diameter in the range from about 0.375 mm to 1.07 mm.

The catheter body will usually be straight along all or most of its length. By "straight" it is meant that the catheter body will assume a straight or linear configuration, when free from external bending forces. The catheter body, however, will be highly flexible so that it will be able to pass through the tortuous regions of a patient's vasculature, as described in more detail herein below. In some cases, the catheter bodies may have a shaped distal end including curves and bends which are selected to facilitate introduction and placement of the catheter (usually over a separate guide wire) in the vascular system. A particular geometry of curves and/or bends may be selected to accommodate the intended use of the catheter.

The catheter body will usually include at least two, and more usually three distinct regions, with each region having a different construction resulting in different mechanical properties. A shaft region extends from the proximal end of the catheter body to a location spaced within 20 cm of the distal end of the catheter body, usually from 2 cm to 6 cm of the distal end. The shaft region will have the maximum reinforcement of the catheter body (including all three layers), thus having most column strength and hoop strength but the least flexibility. A transition region is located immediately on the distal side of the shaft region and extends to a location spaced within 10 cm of the distal end of the catheter body, usually from 1 cm to 3 cm of the distal end. The transition region will have an intermediate level reinforcement (including the inner tubular member and the soft outer layer, but lacking the braided reinforcement layer) together with intermediate levels of column strength, hoop strength, and flexibility. A distal region extends distally from the transition region, and is composed of a soft, unreinforced material. The distal region will generally be relatively short, typically having a length in the range from about 1 cm to 3 cm, and will have the greatest flexibility of the three regions of the catheter body.

In a first alternate embodiment, the braided reinforcement layer terminates at the distal end of the inner tubular member, with the soft outer layer extending distally from 1 cm to 10 cm, preferably from 1 to 3 cm. In a second alternate embodiment, the outer soft layer terminates at the distal end of the inner tubular member, with the braided reinforcement layer terminating proximally of both the outer layer and tubular member by a distance in the range from 1 cm to 10 cm, preferably from 1 cm to 3 cm. In both these embodiments, the catheter has two distinct regions with different mechanical properties.

As a consequence of the preferred fabrication technique, as described in more detail below, the diameters of the transition region and the distal region of the catheter body may be somewhat smaller than that of the shaft region. While such a decrease in geometry in the distal direction may be advantageous, is not essential for the catheters of the present invention. Thus, the present invention includes both catheters having uniform diameters along their entire length and catheters having diameters which decrease in the distal direction.

In a preferred construction, the catheter body of the present invention will consist essentially of three structural components. The first component is an inner tubular member which defines the inner lumen and provides a lubricious surface to receive the fluid or device which is to be introduced to a target location within the vasculature or other body lumen. Typically, the inner tubular member will be a sleeve formed from a single material, preferably a lubricious polymer, such as a fluorocarbon (e.g., polytetrafluoroethylene (PTFE)), a polyamide (e.g., nylon), a polyolefin, a polyimide, or the like. It would also be possible to form the inner tubular members as a laminate structure comprising a non-lubricious outer layer and an inner lubricious layer or coating.

The second structural component of the catheter body is a braided reinforcement layer comprising braided filaments formed directly over the inner tubular member using conventional braiding techniques. The braid filaments will have a very small cross-sectional area while possessing sufficient tensile strength to undergo the braiding process. Preferably, the braid filaments will be composed of stainless steel, a shape memory alloy (e.g., Nitinol®), polymeric fibers, or the like. Particularly preferred are stainless steel filaments having a rectangular cross-section with a width in the range from 0.001 inch to 0.01 inch, preferably being about 0.0025 to 0.005 inch, and a thickness in the range from 0.0002 inch to 0.002 inch, preferably being about 0.0005 to 0.001 inch. Such small filaments can be formed over the inner tubular member in a conventional one-over-one or two-over-two braid pattern, with the machine being carefully adjusted to avoid excessive tensile forces on the filaments.

The third structural component of the catheter body is a soft outer layer which is formed over the braided reinforcement layer and which extends distally of the distal end of the tubular member. The soft outer layer will cover the entire assembly of both the inner tubular member and the braided reinforcement layer, creating the three distinct regions discussed above in connection with the exemplary embodiment. The shaft region will include all three structural components, i.e., the inner tubular member, the braided reinforcement layer formed over the inner tubular member, and the soft outer layer formed over the braided reinforcement layer. The transition region will include both the inner tubular member and the soft outer layer, but will free from the braided reinforcement layer. In this way, the flexibility of the transition region is significantly improved, although the strength characteristics are reduced somewhat when compared to the shaft region. The distal region will consist only of the soft outer layer. The soft outer layer will be formed so that it defines a distal lumen which is contiguous with the central lumen defined by the inner tubular member. Alternate embodiments lacking either of the two distal regions have been described above.

The soft outer layer can be composed of a variety of materials, preferably being composed of a soft thermoplastic material having a hardness in the range from 30 A to 72 D. Exemplary materials include polyamide polyether block copolymer (Pebax®), polyurethanes, silicone rubbers, nylons, polyethylenes, fluoronated hydrocarbon polymers, and the like.

Figure 2:
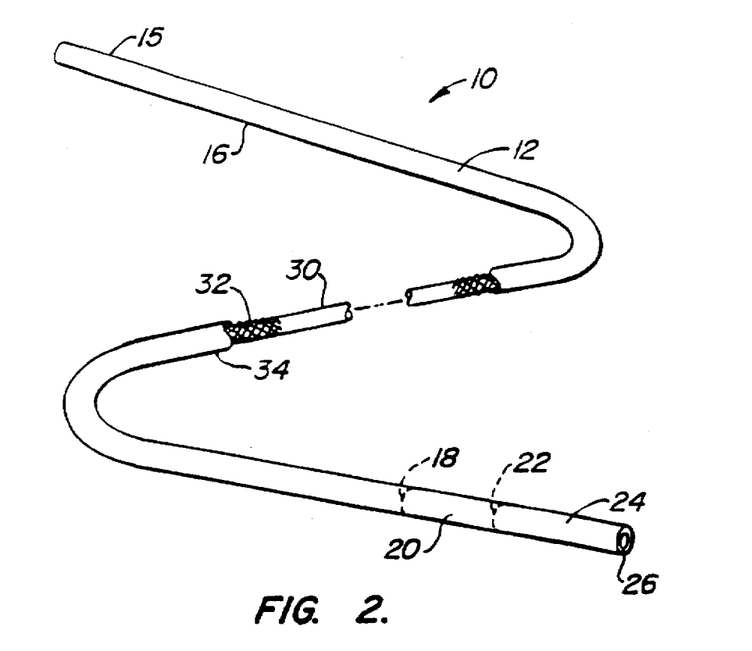
FIG. 2 is a perspective view of the inner catheter of FIG. 1 constructed in accordance with the principles of the present invention, with portions broken away.
Figure 3:
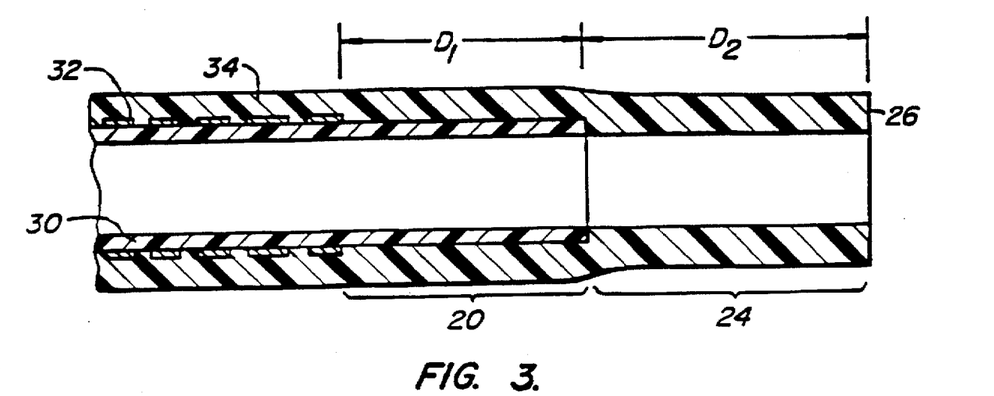
FIG. 3 is an enlarged cross-sectional view of the distal end of the inner catheter of FIG. 2.

Referring now to FIGS. 2 and 3, an inner catheter 10 constructed in accordance with the principles of the present invention includes a catheter body 12. The catheter body 12 includes a shaft region 16 which extends from the proximal end 15 to a distal termination location, indicated by broken line 18. The transition region 20 extends from the termination 18 of the shaft region to a second termination location indicated by broken line 22. A distal region 24 extends from the termination 22 of the transition region 20 to a distal end 26 of the catheter body 12. The transition region 20 will thus have a length $D_1$ in the range from 0 cm to 10 cm, preferably from 1 cm to 10 cm, and more preferably from 1 cm to 3 cm and the distal region 24 will have a length $D_2$ in the range from 0 cm to 10 cm, preferably from 1 cm to 10 cm, and more preferably from 1 cm to 3 cm, as shown in FIG. 2.

The catheter body 12 includes an inner tubular member 30, typically comprising a PTFE tube. Braid structure 32 is then formed over the inner tubular member 30 from the proximal end thereof to near the termination location 18. The braid structure 32 will be square cut, as described in more detail hereinafter, so that it terminates cleanly at the desired termination location and is free from protrusions, burrs, and other discontinuities which could expose the patient to injury. A soft outer layer 34 extends from the proximal end of catheter body 16 to the distal end 26, covering both the inner tubular member 30 and the reinforcement braid 34.

According to a preferred fabrication method, the catheter body 12 may be formed by placing a selected length of PTFE or other tubing over an elongate mandrel. Usually, the mandrel will be coated with PTFE to facilitate introduction and removal of the mandrel to and from the structure being formed. The assembly of the inner tubular member 30 over the mandrel is then introduced to a braiding machine, such as those available from Steeger, Germany; Wardwel, Mass.; and other commercial suppliers, where a conventional one-over-one or two-over-two braid pattern is formed. The pic and other characteristics of the braid will be selected to provide the desired stretch and flexibility for the shaft region. Usually, the pic will be in the range from 20 to 150 pics/inch, preferably from 60 to 100 pics/inch, and the pic may be constant over the entire length of the braided reinforcement layer or may be varied to increase flexibility at or near the distal end of the shaft region. In particular, the braid characteristics such as the pic, cross-sectional area, material strength, and the like, may be varied to provide increased flexibility at the distal end of the catheter body, typically over the distal 1 cm to 60 cm of the catheter body, usually over at least 5 cm, and more usually from 10 cm to 60 cm. The increased flexibility may be constant over the distal end, or may be progressive (i.e., becoming increasingly flexible near the distal end). The use of such non-uniform braid characteristics to enhance flexibility at the distal end of the catheter body is particularly useful when the inner tubular member, reinforcement layer, and soft outer layer are terminated within 1 cm of each other.

In a particular aspect of the fabrication technique of the present invention, the braid is formed over a length which is slightly greater than that desired in the final construction. After forming the braid, the braid will be slipped distally over the inner tubular member so that it extends beyond both the inner tubular member and the mandrel. The stainless steel braid material will then be heat annealed, typically by exposure to a flame or resistance heater, and will thereafter be transversely cut to provide a clean, square-cut distal end. After being cut, the braid is then pulled proximally back over the mandrel and the inner tubular member 30, so that the distal termination 18 of the braid lies at the desired location.

The soft outer layer 34 is then formed over the assembly of the inner tubular member 30 and the braid 32 by placing a thermoplastic tube, typically a Pebax® tube, over the entire assembly so that a distal end of the tube extends distally of the distal end of inner tubular member 30. A heat shrink tube, such as a polyethylene or fluoropolymer tube, is then placed over the soft thermoplastic, and the entire assembly placed in an oven and heated to a temperature sufficient to melt the thermoplastic and constrict the heat shrink tube over the melted thermoplastic. In this way, the thermoplastic material is able to impregnate the braid 32 and is constricted over the mandrel to form a contiguous lumen, as best illustrated in FIG. 3. By carefully choosing the mandrel diameter to match that of the inner diameter of tubular member 30, a very smooth transition between the lumen of inner tubular member 30 and that defined by the soft outer layer 26 can be obtained.

After cooling, the heat shrink tube can be cut from the catheter body assembly. The distal end of a soft outer layer can then be cut to its desired final length. The proximal connector 14 can then be attached to the proximal end of the catheter body 12, although the connector is not an essential part of the present invention.

Inner catheter 10 can be further modified by providing radiopaque markers at one or more locations along its length. Such radiopaque markers can comprise metal rings, or can be defined by impregnating the soft polymeric layer with appropriate radiopaque dyes. The provision of radiopaque markers is well known in the art and does not form a part of the present invention.

Balloon 8 is bonded distal end 5 of sheath 3. Distal end 5 is a necked-down region to reduce outside diameter after annular end 42 of balloon is attached. Balloon 8 is mounted to outer sheath end 5 using an adhesive such as an RTV silicone adhesive, for example Loctite 5140 or Nusil Technology R-1140, or a UV curing adhesive. As shown in FIG. 3, the tip 44 body 12 extends beyond the distal end of sleeve 40; the distal annular edge 46 of elastomeric balloon 8 is bonded to tip 44 using the same or a similar adhesive as used with end 42.

Injection port assembly 6 includes an injection port 48 fluidly coupled to an inflation passageway 50 defined between outer sheath 3 and inner catheter 10. An inflation medium, such as air, contrast fluid, saline, etc., can be injected through port 48, into passageway 50 and out through an annular exit opening 52 defined between distal end 5 of sheath 3 and distal region 24 of catheter body 12. Doing so causes balloon 8 to expand to either partially or totally occlude the particular vessel within which the balloon has been placed. Total occlusion of the vessel can be desired for, for example, diagnostic purposes or to permit injection of saline to promote successful use of endoscopic devices. Partial occlusion can be useful when injecting particles, tissue adhesives or coils, when placing detached balloons and when conducting diagnostic procedures and other therapeutic procedures.

Balloons having minimum and maximum diameters from about 4 to 14 mm can be used with inner catheter/outer sheath sizes from about 3.2 F/5.5 F to about 7 F/9.5 F. Balloons having minimum and maximum diameters from about 2 to 7 mm can be used with inner catheter/outer sheath sizes from about 1 F/3 F to about 3.2 F/6.5 F.

Although not shown in the figures, it is preferred to secure inner catheter 10 to outer sheath 3 at several places, typically three, in addition to their distal ends (through balloon 8) and their proximal ends (through injection port assembly 16). This can be accomplished by staking outer sheath 3 against inner catheter at several positions in a manner not to seal off passageway 50. Alternatively, outer layer 34 can be made with raised buttons or beads of material extending from the outer surface of outer layer 34; after assembly, sheath 3 can be heat sealed to outer layer 34 of inner catheter 10 at the beads or buttons, again while maintaining free fluid flow along passageway 50.

Outer sheath 3 can be further modified for particular uses. For example, small perfusion ports or holes can be formed near distal end 5 to facilitate liquid perfusion, e.g., drug delivery, using catheter 2. Coatings such as hydrophilic, anti-thrombogenic, low-friction, hydrophobic, and other, coatings can be placed over the outer surface of the outer sheath 3 to enhance its use for particular applications. Additionally, distal end 5 can be formed into a desired geometry.

One specific treatment the present invention is especially suited for is treating aneurysms. An aneurysm is the thinning of a wall of a blood vessel; if the blood vessel is within the brain and the thin wall bursts, a stroke can result. One way to prevent bursting of the vessel is to halt the flow of blood just upstream of the aneurysm. However, before doing so, it is best to determine what the effects of the blockage will be. That is, will blockage of the vessel create more problems than it solves by, for example, causing the patient to lose his or her eyesight or the ability to walk. In the past, blood vessels were temporarily occluded by the insertion of a balloon at a distal end of a catheter. If the effects were acceptable, the balloon catheter would be removed and a therapeutic catheter would be inserted in its place. Some type of occlusion mechanism, typically tissue adhesives or a physical obstruction, would typically be inserted to occlude the vessel and thus prevent the stroke. However, balloon catheter 2 provides for both the occlusion of the vessel by elastomeric balloon 8 and an open inner passageway through inner catheter 10 for carrying out the appropriate therapy. Therefore, there is no need to switch catheters with the present invention.

Figure 4:
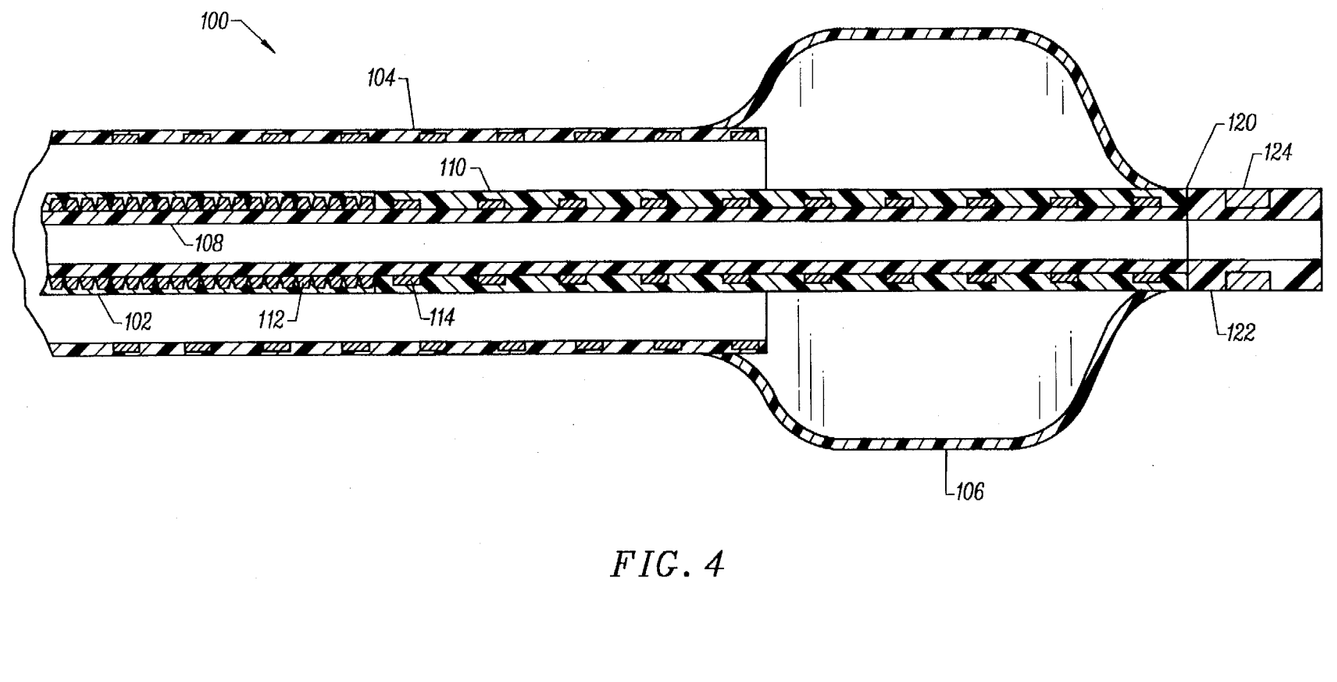
FIG. 4 is a simplified side view of an alternative embodiment of the balloon catheter of the present invention, shown in cross-section.

An alternative embodiment 100 of the balloon catheter of the present invention is illustrated in FIG. 4. Balloon catheter 100 comprises an inner catheter 102, an outer sheath 104, and a balloon 106. Portions of the catheter 100 proximal to those illustrated may be identical to catheter 2 illustrated in FIG. 1.

The inner catheter 102 comprises inner tubular member 108 and a soft outer layer 110, both of which elements are constructed similarly to those found in catheter 2. Inner catheter 102, in contrast to the prior described embodiments, includes a first reinforcement layer 112 and a second reinforcement layer 114, where the first reinforcement layer provides greater stiffness or column strength than does the second reinforcement layer 114. Preferably, the first reinforcement layer will be formed as a braided ribbon structure, generally as for the reinforcement layer in previously described embodiments. The second reinforcement layer 112, in contrast, will preferably be a helically wound ribbon, where the individual turns of the ribbon are axially spaced-apart by a short distance to enhance flexibility. Usually, the ribbon of the second reinforcement layer 114 will be a stainless steel ribbon. Also, the second reinforcement layer 114 will usually extend fully to the distal end 120 of the inner catheter 102.

The outer sheath 104 will preferably be reinforced, typically by a helically wound ribbon, such as a stainless steel ribbon having cross-sectional dimensions of about 0.001 inch by 0.005 inch. The sheath 104 will typically be composed of pebax.

The balloon is preferably an elastomeric balloon typically composed of a urethane-based material. Such a balloon will be highly compliant. As illustrated in FIG. 4, the balloon 106 will be attached at its proximal end to the distal end of the sheath 104 and at its distal end to the distal end of the catheter 102.

In the preferred embodiment, a separate, soft distal tip 122 will be attached to the distal end of the inner catheter 102. Usually, a radiopaque marker, such as the marker ring 124, will be embedded within the soft tip 122.

Although the foregoing invention has been described in detail for purposes of clarity of understanding, it will be obvious that certain modifications may be practiced within the scope of the appended claims.

What is claimed is:

1. A balloon catheter comprising:
   an inner catheter, having proximal and distal ends, comprising:
   an inner tubular member having a proximal end, a distal end, and a lumen extending from the proximal end to the distal end;
   a braided reinforcement layer disposed over the inner tubular member and having a proximal end and a distal end, wherein the distal end of the braided reinforcement layer terminates at a distance in the range from 3 cm to 10 cm proximally from the distal end of the inner tubular member; and
   a soft outer layer formed over the braided reinforcement layer and extending distally to the distal end of the inner tubular member;
   an outer sheath extending coaxially over the inner catheter and having a distal end and a proximal end, wherein the distal end terminates distally of the distal end of the braided reinforcement layer;
   an injection port at the proximal end of the outer sheath;
   a balloon mounted to and generally circumscribing the distal ends of the inner catheter and the outer sheath; and
   an inflation passageway defined between the outer sheath and the inner catheter and fluidly coupling the injection port and the balloon whereby the balloon can be inflated through the injection port.

2. A balloon catheter as in claim 1, wherein the inner tubular member is composed of a material selected from the group consisting of fluorocarbons, polyamides, polyolefins, and polyimides.

3. A balloon catheter as in claim 2, wherein the inner tubular member is polytetrafluoroethylene.

4. A balloon catheter as in claim 1, wherein the braided reinforcement layer comprises at least one stainless steel braid formed over the inner tubular member.

5. A balloon catheter as in claim 4, wherein the distal end of the stainless steel braid has been annealed and transversely cut to remove protrusions.

6. A balloon catheter as in claim 1, wherein the soft outer layer is composed of a material having a hardness in the range from 30 A to 72 D.

7. A balloon catheter as in claim 6, wherein the material is selected from the group consisting of polyether block copolymer, polyurethane, silicone rubber, nylon, polyethylene, and fluoronated hydrocarbon polymers.

8. A balloon catheter as in claim 1, wherein the soft outer layer is impregnated into the braided reinforcement layer.

9. A balloon catheter as in claim 1, further comprising a connection fitting at the proximal end of the inner tubular member, braided reinforcement layer, and soft outer layer.

10. A balloon catheter as in claim 1 wherein the inflation passageway is an annular passageway.

11. A balloon catheter as in claim 1 wherein the balloon is an elastomeric balloon.

12. A balloon catheter comprising:
   an inner catheter having a proximal end, a distal end, and a lumen therebetween, wherein the inner catheter includes a first reinforcement layer extending from a proximal end thereof to a transition point and a second reinforcement layer extending from the transition point to near the distal end thereof, said second reinforcement layer being less stiff than the first reinforcement layer;
   an outer sheath formed coaxially over the inner catheter and extending from the proximal end of the inner catheter to a point over the second reinforcement layer;
   a balloon attached to the distal ends of the outer sheath and inner catheter so that said balloon can be inflated through an annular lumen formed between the outer sheath and inner catheter and;
   an unreinforced soft tip secured to and extending from the distal end of the inner catheter.

13. A balloon catheter as in claim 12, wherein the first reinforcement layer is a braided ribbon structure and the second reinforcement layer is a helically wound ribbon structure.

14. A balloon catheter as in claim 12, wherein the outer sheath includes a reinforcement layer.

15. A balloon catheter as in claim 14, wherein the sheath reinforcement layer comprises a helically wound ribbon structure.

16. A balloon catheter as in claim 12, wherein the inner catheter further comprises an inner tubular member and a soft outer layer formed over the inner tubular member, wherein the reinforcement layers are disposed over the outer surface of the inner tubular member and embedded within the soft outer layer.

17. A balloon catheter as in claim 16, wherein the inner tubular member, the second reinforcement layer, and the outer soft layer all terminate at the distal end of the inner catheter.

18. A balloon catheter comprising:
   an inner catheter having a proximal end, a distal end, and a lumen therebetween;
   an outer sheath formed coaxially over the inner catheter and extending from the proximal end thereof to a point spaced proximally from the distal end thereof, wherein the outer sheath includes a reinforcement layer consisting of a helically wound ribbon; and
   a balloon attached to the distal ends of the outer sheath and inner catheter so that said balloon can be inflated through an annular lumen formed between the outer sheath and inner catheter.

19. A balloon catheter as in claim 18, wherein the inner catheter includes a first reinforcement layer extending from a proximal end thereof to a transition point and a second reinforcement layer extending from the transition point to near the distal end thereof, said second reinforcement layer being less stiff than the first reinforcement layer.

20. A balloon catheter as in claim 19, wherein the first reinforcement layer is a braided ribbon structure and the second reinforcement layer is a helically wound ribbon structure.

21. A balloon catheter as in claim 20, wherein the inner catheter further comprises an inner tubular member and a soft outer layer formed over the inner tubular member, wherein the reinforcement layers are disposed over the outer surface of the inner tubular member and embedded within the soft outer layer.

22. A balloon catheter as in claim 21, wherein the inner tubular member, the second reinforcement layer, and the outer soft layer all terminate at the distal end of the inner catheter.

23. A balloon catheter comprising:

an inner catheter having a braid-reinforced proximal region and a helical coil reinforced distal transition region, wherein the transition region is less stiff than the proximal region;

an outer sheath coaxially received over the inner catheter, wherein a distal end of the sheath terminates over the transition region of the inner catheter;

an elastomeric balloon attached to and generally circumscribing the distal ends of the inner catheter and the outer sheath; and a soft distal tip secured to the distal end of the inner catheter and extending beyond the balloon.

24. A balloon catheter as in claim 23, wherein the outer sheath includes a reinforcement layer.

25. A balloon catheter as in claim 23, wherein the inner catheter comprises an inner tubular member and a soft outer layer formed over the inner tubular member, wherein the reinforcing braid and helical coil are disposed over the inner tubular member and embedded within the soft outer layer.

26. A balloon catheter as in claim 25, wherein the inner tubular member, the helical coil reinforcement, and the soft outer layer all terminate at the distal end of the inner catheter.

27. A balloon catheter comprising:

an inner catheter having a braid-reinforced proximal region and a helical coil reinforced distal transition region, wherein the transition region is less stiff than the proximal region;

an outer sheath having helical coil reinforcement and being coaxially received over the inner catheter, wherein a distal end of the sheath terminates over the transition region of the inner catheter;

an elastomeric balloon attached to and generally circumscribing the distal ends of the inner catheter and the outer sheath; and a soft distal tip secured to the distal end of the inner catheter and extending beyond the balloon.

* * * * *